United States Patent [19]

Slusarek et al.

[11] Patent Number: 5,055,385

[45] Date of Patent: Oct. 8, 1991

[54] PHOTOGRAPHIC ELEMENTS CONTAINING RELEASE COMPOUNDS-II

[75] Inventors: Wojciech Slusarek; John M. Buchanan; Philip T. S. Lau, all of Rochester, N.Y.

[73] Assignee: Eastman Kodak Company, Rochester, N.Y.

[21] Appl. No.: 670,082

[22] Filed: Mar. 15, 1991

Related U.S. Application Data

[63] Continuation-in-part of Ser. No. 614,810, Nov. 16, 1990.

[51] Int. Cl.$^5$ ............................ G03C 7/32; G03C 7/42
[52] U.S. Cl. ..................................... 430/544; 430/223; 430/543; 430/549; 430/955; 430/957; 430/958; 430/959

[58] Field of Search ............... 430/223, 543, 544, 549, 430/955, 957, 958, 959

[56] References Cited

U.S. PATENT DOCUMENTS

| | | | |
|---|---|---|---|
| 4,248,962 | 2/1981 | Lau | 430/382 |
| 4,409,323 | 10/1983 | Sato et al. | 430/544 |
| 4,678,735 | 7/1987 | Kitaguchi et al. | 430/203 |
| 4,684,604 | 8/1987 | Harder | 430/375 |
| 4,775,610 | 10/1984 | Kitaguchi et al. | 430/350 |
| 4,861,701 | 8/1989 | Burns et al. | 430/543 |

*Primary Examiner*—Richard L. Schilling
*Attorney, Agent, or Firm*—Joshua G. Levitt

[57] ABSTRACT

There are described color photographic elements containing novel release compounds which rapidly release a photographically useful group, such as a development inhibitor, from a timing group.

12 Claims, No Drawings

PHOTOGRAPHIC ELEMENTS CONTAINING RELEASE COMPOUNDS-II

This invention relates to silver halide color photographic elements containing novel release compounds.

Images are formed in silver halide color photographic materials by reaction between oxidized silver halide developing agent, resulting from the imagewise reduction of silver halide to metallic silver, and a dye-forming compound known as a coupler. It has become common practice to modify photographic properties of the image, such as sharpness, granularity and contrast, by the use of a image modifying compound commonly referred to as a development inhibitor releasing (DIR) coupler. Such materials were first described in U.S. Pat. Nos. 3,148,062 and 3,227,554.

More recently, U.S. Pat. Nos. 4,248,962; 4,409,323; 4,684,604; and European Patent Application 0 167 168 have described release compounds from which a development inhibitor is released from an intervening group, called a timing group, after that group is released from the carrier portion of the compound. The use of a timing group provides a way to separate the release function from the photographic function and permits these separate functions to be designed into the compound in an optimal manner. Thus, control over the rate, location and time of the release of the development inhibitor can be optimized by the use of a separate timing group.

In addition to development inhibitors other photographically useful groups may desirably be released during photographic processing. Such groups include development accelerators, complexing agents, toners, stabilizers etc. While photographically useful groups typically are released during the development step in an imagewise manner, occasionally it is desired to release a photographically useful group uniformly. This is accomplished by blocking an active site of the photographically useful group with a blocking group that will be cleaved therefrom uniformly under processing conditions.

In U.S. Pat. No. 4,409,323 are described a class of release compounds that contain what has been referred to as a "quinone methide" timing group. While these release compounds are desirable for a number of purposes, the rate at which they release a number of photographically useful groups is not optimum. This is particularly true with photographically useful groups containing nitrogen heterocycles.

Accordingly, it would be desirable to provide release compounds and photographic elements containing them which release photographically useful groups from quinone methide-type timing groups in an optimum manner.

We have found that this can be accomplished with a release compound containing a novel timing group. In accordance with this invention there is provided a photographic element comprising a support bearing a silver halide emulsion layer having associated therewith an image dye forming coupler and a release compound represented by the formula:

$$\begin{array}{c} \text{CAR} \\ | \\ \text{TIME} \\ | \\ \text{PUG} \end{array} \qquad \text{I}$$

wherein
CAR is a carrier group from which the remainder of the molecule is released during photographic processing;

PUG is a photographically useful group; and

TIME is a timing group which is released from CAR during photographic processing and subsequently releases PUG, and contains a ring system represented by the structure

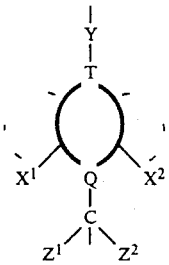

II wherein
T is

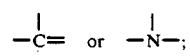

Y is —O—, —S— or

when T is

and Y is

or a covalent bond when T is

Q represents the atoms selected from carbon, nitrogen, oxygen, sulfur and phosphorus to complete a 5-, 6- or 7-membered carbocycle or heterocycle;

$R^1$ is $COR^2$ or $SO_2R^2$;

$R^2$ is alkyl or aryl;

each of $Z^1$ and $Z^2$ is individually hydrogen, alkyl, perfluoroalkyl, aryl, heterocyclyl, $OR^2$, $SR^2$, or $N(R^2)_2$;

each of $X^1$ and $X^2$ is individually a group as defined for $Z^1$ and $Z^2$ or represents the atoms selected from carbon, nitrogen, sulfur and phosphorus to complete a heterocyclic or non-aromatic carbocyclic ring system fused to the ring completed by Q;

with the proviso that each of $X^1$ and $X^2$ and each of $Z^1$ and $Z^2$ is not hydrogen at the same time.

In a preferred embodiment $X^1$ and $X^2$ are individually selected from the groups defined for $Z^1$ and $Z^2$.

In the above structure I, Y is joined to CAR directly or through an intervening timing group and the unsatisfied bond in the carbon atom,

is joined to PUG directly or through an intervening timing group. CAR can be a blocking group formed from a silyl group or from a carboxylic, sulfonic, phosphonic, or phosphoric acid derivative, and which releases —TIME—PUG in a non-imagewise manner by hydrolysis. A preferred such blocking group is described in Buchanan et al, European Patent Application No. 394,974.

Alternatively, CAR can be an oxidizable moiety, such as a hydrazide or hydroquinone derivative, which releases —TIME—PUG in an imagewise manner as a function of silver halide development. Such blocking groups are described, for example, in U.S. Pat. Nos. 3,379,529 and 4,684,604.

In a preferred embodiment of this invention, CAR is a coupler moiety to whose coupling position —TIME—PUG is attached, so that it is coupled off by reaction with oxidized color developing agent formed in an imagewise manner as a function of silver halide development. When CAR is divalent, multivalent, or polymeric, it is capable of releasing more than one —TIME—PUG moiety. To immobilize CAR—TIME—PUG when it is incorporated in a photographic element, a ballast group may be attached to either, or both of the CAR and TIME moieties.

TIME represents a ring system shown above, comprising one to three rings. In the cases of two or three rings, each ring shares two of its members with an adjacent ring. This ring system contains one or more double bonds so arranged as to provide a pathway for electron transfer along a conjugated system allowing bond cleavage necessary to release PUG. The TIME group can, in addition to the fused ring system shown above, contain one or more additional timing groups, so as to provide a double or multiple switch timing group as described in Burns and Taber U.S. Pat. No. 4,861,701.

PUG is a photographically useful group made available during processing by release from TIME. PUG can be a dye or dye precursor, such as a sensitizing dye, filter dye, image dye, leuco dye, blocked dye, shifted dye, or ultraviolet light absorber. Alternatively PUG can be a photographic reagent, which upon release can further react with components in the element. Such reagents include development accelerators, development inhibitors, bleach accelerators, bleach inhibitors, couplers (e.g. competing couplers, color-forming couplers, or DIR couplers), developing agents (e.g. competing developing agents or auxiliary developing agents), silver complexing agents, fixing agents, toners, hardeners, tanning agents, fogging agents, antifoggants, antistain agents, stabilizers, nucleophiles and dinucleophiles, and chemical or spectral sensitizers and desensitizers.

We have found that the timing groups of this invention release nitrogen heterocycle inhibitors at a rate that permits their effective use in a photographic element. Thus, PUG is preferably a development inhibitor and most preferably is a nitrogen heterocycle such as a triazole, tetrazole, pyrazole, and the like.

In the ring system which forms a part of the structure I shown above, Q can complete a carbocyclic or heterocyclic ring or ring system. Rings completed by Q include derivatives of benzene, naphthalene, pyridinone, quinoline, imidazole, pyrazole, and the like. Preferably Q completes a phenylene ring. Q can be substituted with non-interfering electron withdrawing or electron donating substituents such as halogen, nitro, sulfono, alkyl, alkoxy, alkylthio, arylthio, aryloxy, aryl, amido, sulfonamide, and the like.

In the structures shown herein, alkyl groups and the alkyl portions of alkyl-containing substituents can contain up to 20 carbon atoms and can be substituted with such groups as halogen, carboxy, amido, sulfonamido, and the like. In instances where bulk is not desired, or is detrimental, the alkyl group would contain 1 to 4 carbon atoms. Aryl groups and the aryl portion of aryl-containing substituents include phenyl, naphthyl and anthracyl groups which can be unsubstituted or substituted with substituents as described above for the alkyl group, or with alkyl groups. Representative heterocyclic groups include pyridyl, quinolyl, pyrazolyl, furanoyl, thiophenyl, and the like. Representative fused rings completed by $X^1$ and $X^2$ include cyclopenteno, cyclohexeno, furano, pyrano and morpholino.

In a preferred embodiment of this invention, TIME includes the ring system represented by the structure:

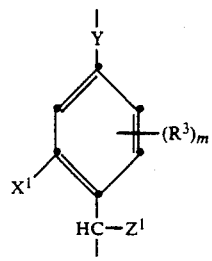

III wherein

Y is —O— or —S—;

$R^3$ is a non-interfering substituent selected from electron withdrawing groups and electron donating groups;

m is 0, 1, 2, or 3; and $X^1$ and $Z^1$ are independently alkyl, alkoxy, alkylthio, aryl, aryloxy, arylthio or heterocyclyl.

As indicated above, preferred CAR groups are couplers. Most preferably Y in structures II and III above are joined directly to the coupling position of the coupler moiety. The coupler moiety can be any coupler that forms a colored or colorless, diffusible or nondiffusible reaction product with oxidized silver halide developing agent. Representative coupler moieties are derived from phenol, naphthol, pyrazolone, pyrazoloazole, and acylacetamide couplers by replacing the atom in the coupling position of the coupler with the remainder of the molecule.

Structures of representative TIME groups of the invention are as follows:

(1) 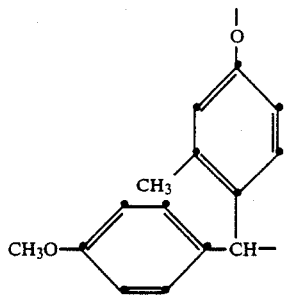
(2) 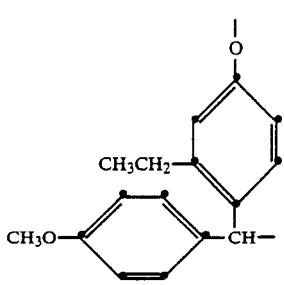
(3) 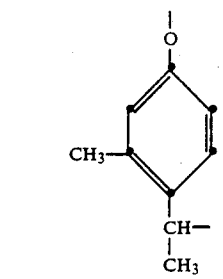
(4) 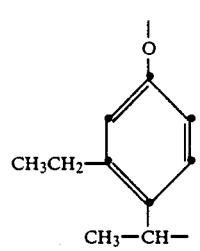
(5) 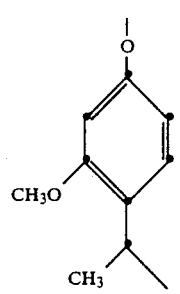
(6) 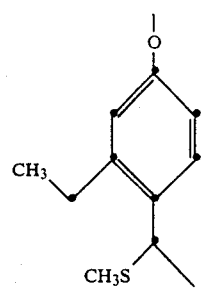
(7) 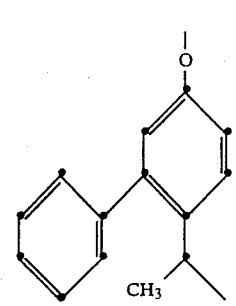
(8) 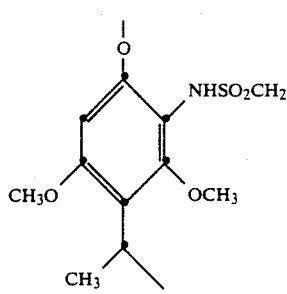
(9) 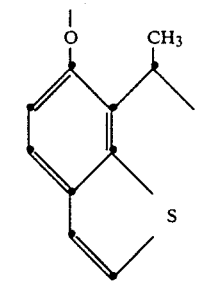
(10) 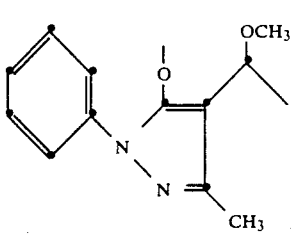

(11) 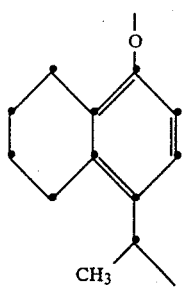
(12) 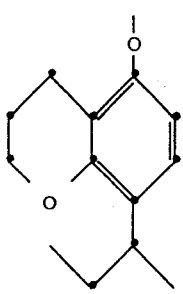
(13) 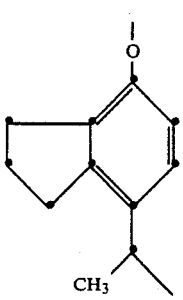
(14) 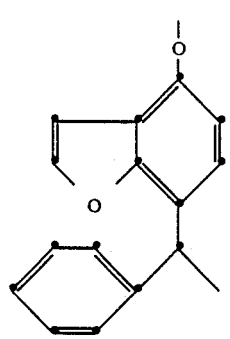
(15) 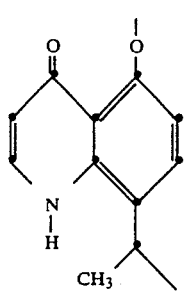
(16) 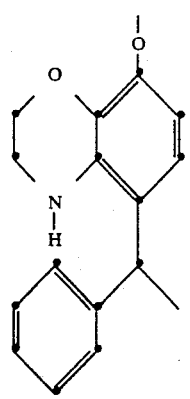
Structures of representative couplers of this invention are as follows:
(17) 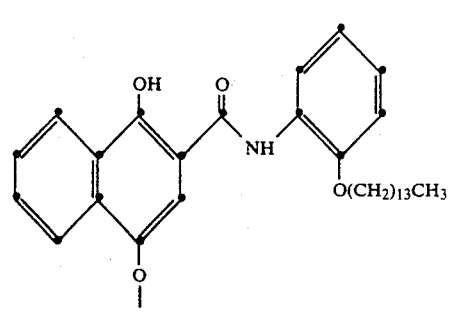
(18) 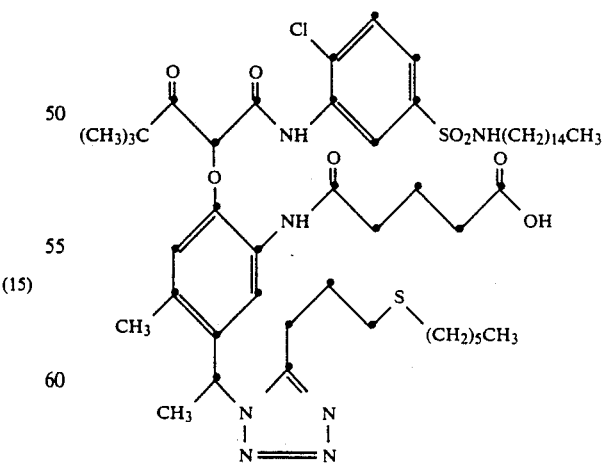
The compounds employed in this invention can be prepared by synthetic procedures well known in the art. Generally, this involves first the preparation of a suitable precursor of the timing group followed by its attachment to the carrier group. The photographically useful group is then connected to the timing group. The release compounds can be used and incorporated in photographic elements in the way that such compounds have been used in the past. Depending upon the nature of the particular photographically useful group, the release compound can be incorporated in a photographic element for different purposes and in different locations and these elements can contain various other components. Reference will be made to exemplary ways in which preferred photographically useful groups can be incorporated.

When the photographically useful group released is a development inhibitor, it can be employed in a photographic element as described, for example, in U.S. Pat. Nos. 3,227,554; 3,620,747; 3,703,375; 4,248,962 and 4,409,323. Compounds of this invention which release a development inhibitor can be contained in, or in reactive association with, one or more of the silver halide emulsion units in a color photographic element. If the silver halide emulsion unit is composed of more than one layer, one or more of such layers can contain the compound of this invention. The layers can contain other photographic couplers conventionally used in the art. The couplers of this invention can form dyes of the same color as the color forming coupler(s) in the layer or unit, it can form a dye of a different color, or it can result in a colorless or neutral reaction product. The range of operation of the development inhibitor between layers when released from the coupler of this invention can be controlled by the use of scavenger layers, such as a layer of a fine grain silver halide emulsion. Scavenger layers can be in various locations in an element containing couplers of this invention. They can be located between layers, between the layers and the support, or over all of the layers.

Release compounds of this invention which release bleach inhibitors can be employed in the ways described in U.S. Pat. No. 3,705,801, to inhibit the bleaching of silver in selected areas of a photographic element.

Release compounds of this invention which release a dye or dye precursor can be used in processes where the dye is allowed to diffuse to an integral or separate receiving layer to form a desired image as described for example in U.S. Pat. Nos. 3,227,551; 3,443,940 and 3,751,406. Alternatively, the dye can be retained in the location where it is released to augment the density of the dye formed from the coupler from which it is released or to modify or correct the hue of that dye or another dye. In another embodiment, the released dye can be completely removed from the element and the dye which was not released from the coupler can be retained in the element as a color correcting mask.

Release compounds of this invention in which the photographically useful group is a coupler can be employed to release another coupler. If the released coupler is a dye-forming coupler it can react with oxidized developing agent in the same or an adjacent layer to form a dye of the same or a different color or hue as that obtained from the primary coupler. If the released coupler is a competing coupler it can react with oxidized color developing agent in the same or an adjacent layer to reduce dye density.

Release compounds of this invention in which the photographically useful group is a developing agent can be used to release a developing agent which will compete with the color forming developing agent, and thus reduce dye density. Alternatively, they can provide, in an imagewise manner, a developing agent which because of such considerations as activity would not desirably be introduced into the element in a uniform fashion.

Release compounds of this invention in which the photographically useful group is a nucleating agent, can be used to accelerate development.

The photographic elements can be single color elements or multicolor elements. Multicolor elements typically contain dye image-forming units sensitive to each of the three primary regions of the visible spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer, e.g., as by the use of microvessels as described in Whitmore U.S. Pat. No. 4,362,806 issued Dec. 7, 1982.

In the following discussion of suitable materials for use in the emulsions and elements of this invention, reference will be made to *Research Disclosure*, December 1989, Item 308119, published by Kenneth Mason Publications, Ltd., Dudley Annex, 12a North Street, Emsworth, Hampshire P010 7DQ, ENGLAND, the disclosures of which are incorporated herein by reference. This publication will be identified hereafter by the term "Research Disclosure".

The silver halide emulsions employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers generally described above, the elements of the invention can include additional couplers as described in Research Disclosure Section VII, paragraphs D, E, F and G and the publications cited therein. These couplers can be incorporated in the elements and emulsions as described in Research Disclosure Section VII, paragraph C and the publications cited therein.

The photographic elements of this invention or individual layers thereof, can contain brighteners (see Research Disclosure Section V), antifoggants and stabilizers (See Research Disclosure Section VI), antistain agents and image dye stabilizers (see Research Disclosure Section VII, paragraphs I and J), light absorbing and scattering materials (see Research Disclosure Section VIII), hardeners (see Research Disclosure Section IX), plasticizers and lubricants (See Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative working silver halide, the processing step described above gives a negative image. To obtain a positive (or reversal) image, this step can be preceded by development with a non-chromogenic developing agent to develop exposed silver halide, but not form dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following preparative examples illustrate preparation of release compounds of this invention.

PREPARATIVE EXAMPLE 1

Preparation of Compound 17

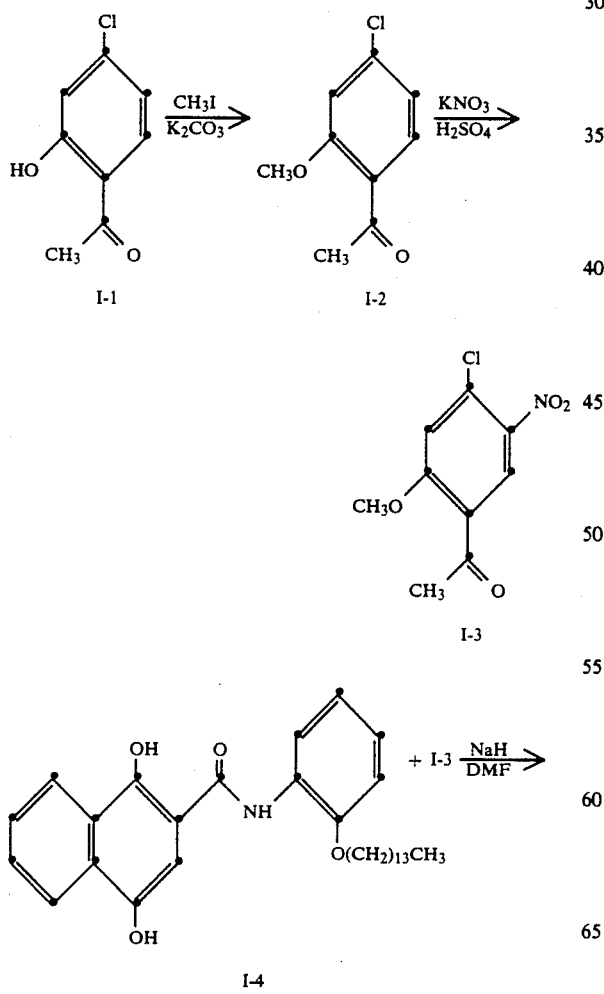

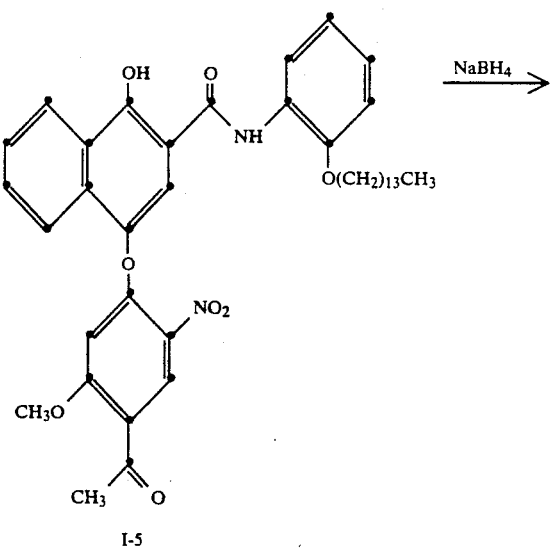

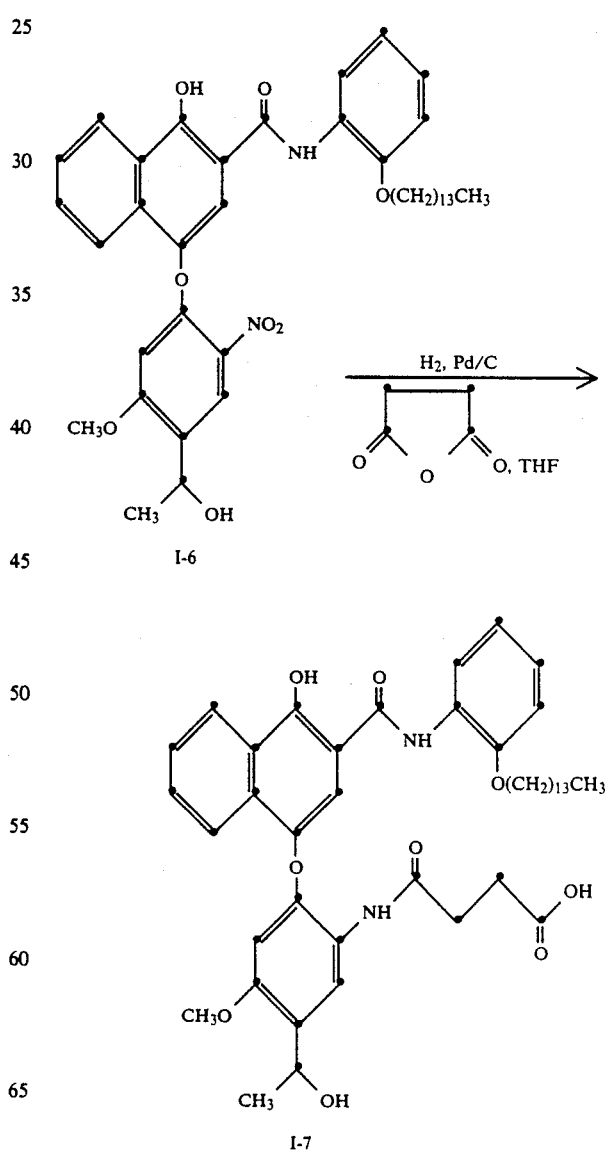

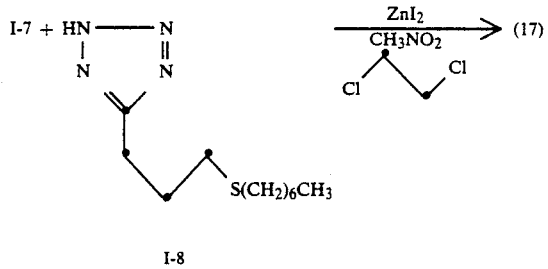

I-8

Preparation of I-2

A solution of 4-chloro-2-hydroxyacetophenone (I-1, 77 g, 0.45 mole) and methyl iodide (96 g, 0.68 mole) in 1500 ml of butan-2-one was refluxed in the presence of potassium carbonate (93 g, 0.68 mole) for 24 h. The mixture was then cooled to room temperature and filtered. The filtrate was taken to dryness and the residue recrystallized from ligroin. Yield 57 g (69%) of I-2.

Preparation of I-3

To a solution of I-2 (52 g, 0.28 mole) in 600 ml of sulfuric acid was added at 5° C. a solution of potassium nitrate (31 g, 0.31 mole) in 250 ml of sulfuric acid over a period of 30 min. The solution was then stirred at room temperature for 2 h and poured onto ice giving the crude product. One recrystallization from ethanol yielded 43 g (67%) of I-3.

Preparation of I-5

To a slurry of 60% sodium hydride (14 g, 0.42 mole) in 500 ml of dimethylformamide was added at 5° C. a solution of I-4 (85 g, 0.17 mole) in 300 ml dimethylformamide over a period of 30 min. Next, a solution of I-3 (40 g, 0.17 mole) in 300 ml of dimethylformamide was added in drops over a period of 30 min. The reaction mixture was kept at room temperature for 18 h and diluted with ethyl acetate. The solution was washed with dil. hydrochloric acid, brine, dried over magnesium sulfate and filtered. The filtrate was concentrated and passed through a column of silica gel to give 60 g (50%) of I-5.

Preparation of I-6

To a solution of I-5 (6.8 g, 10 mmole) in 150 ml of tetrahydrofuran-isopropanol (1:1) was added sodium borohydride (0.7 g, 18 mmole). The mixture was stirred at room temperature for 24 h and quenched with ice/conc. hydrochloric acid. The precipitated product was collected, washed with water, methanol and dried in vacuo. The yield: 6.3 g (97%) of I-6.

Preparation of I-7

A solution of I-6 (13.7 g, 20 mmole) and succinic anhydride (3.0 g, 30 mmole) in 100 ml of tetrahydrofuran was hydrogenated over 5% palladium on carbon in a pressure bottle. After 10 h the mixture was filtered, the filtrate concentrated and passed through a column of silica gel giving 6.0 g of I-7 (40%).

Preparation of (17)

To a solution of I-7 (2.0 g, 2.6 mmole) and I-8 (0.6 g, 2.6 mmole) in 50 ml of nitromethane and 50 ml dichloroethane was added zinc iodide (0.4 g, 1.3 mmole) and the mixture was stirred at room temperature for 24 h. The reaction was worked up with dil. hydrochloric acid and ether. The ethereal extracts were dried over magnesium sulfate and concentrated in vacuo. The crude product was chromatographed on silica gel giving 1.0 g (40%) of 17, mp 109° C.

Elemental analysis: Calculated: S3.27%, N8.56%, C67.32%, H7.81%. Found: S3.07%, N8.37%, C68.03%, H7.89%.

EXAMPLE 1

Release of an N-containing Development Inhibitor

Rates of tetrazole release were measured for several timing group compounds which are representative of fragments that are generated by reaction of a coupler of this invention with oxidized developer during photographic processing. These solution measurements are a useful indication of photographic performance. Lower values of inhibitor release half-lives in solution correlate with greater development inhibition effects in film.

For a given measurement, 12.5 μmol of the timing group compound was dissolved in 3.2 mL of reduced Triton X-100 surfactant plus one drop glacial acetic acid plus approximately 5 mL methylene chloride (to facilitate dissolution of the timing group compound in surfactant). After methylene chloride was evaporated under partial vacuum, water (approximately 15 mL) was added and the mixture was vigorously agitated with a vortex mixer to create micelles. The micellar solution was then diluted to 25 mL with water and mixed again. Inhibitor release kinetics were initiated by mixing 2 mL of the above micellar solution with an equal volume of an aqueous potassium hydroxide solution (0.75 mol KOH/L), producing a reaction mixture with a pH of about 13.5. At intervals, portions of the reaction mixture were quenched by the addition of 1 mL 30% aqueous acetic acid. The quenched mixture was then analyzed by high performance liquid chromatography to determine the concentrations of free inhibitor and residual timing group compound. First-order reaction rate constants were calculated from these concentration versus time data, and the reaction half-like, $t_{\frac{1}{2}}$, was calculated with the expression $t_{\frac{1}{2}} = 0.693/k$, where k is the observed rate constant. As is evident from the half-lives in Table I, compounds of the invention exhibited inhibitor release half-lives significantly shorter than that for the comparison compound.

In these structures the inhibitor (INH) released was

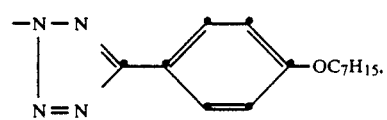

and inventive comparison compounds had the structure shown in Table I.

TABLE I

General Structure

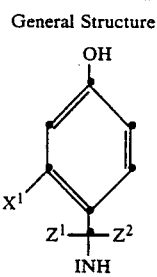

| $X^1$ | $Z^1$ | $Z^2$ | Compound No. | Half-Life at pH 13.5 (sec) |
|---|---|---|---|---|
| —H | —CH$_3$ | —H | C-1 Comparison | 720 |
| —CH$_3$ | —H | —H | C-2 Comparison | 1100 |
| —H | —Ph | —H | C-3 Comparison | 360 |
| —CH$_3$ | p-(MeO)Ph | —H | 1 | 37 |
| —CH$_2$CH$_3$ | p-(MeO)Ph | —H | 2 | 46 |
| —CH$_3$ | —CH$_3$ | —H | 3 | 110 |
| —OCH$_3$ | —CH$_3$ | —H | 5 | 59 |

EXAMPLE 2

Release compounds of this invention were incorporated in a photographic elements having the structure shown below. (The numbers following the dash "-" represent the coverage in g/m$^2$)

| Overcoat: | Gelatin - 5.3; |
| | Bisvinylsulfonyl methyl ether hardener - 2% of total gel |
| Causer Layer: | Gelatin - 2.7; |
| | Green Sensitized AgBrI (6.4 mol percent I; 0.46μ diameter) - 1.6; |
| | Cyan dye-forming coupler A - 0.8; |
| | Release compound-See Table 2 below |
| Interlayer: | Gelatin - 0.9; |
| | Scavenger for oxidized developer - 0.1 |
| Receiver Layer: | Gelatin - 2.4; |
| | Red sensitized AgBrI (6.4 mol percent I; 0.46μ diameter) - 1.6; |
| | Yellow dye-forming coupler B - 1.3 |
| AH Layer: | Gelatin - 2.4; |
| | Grey Silver - 0.3 |
| Polyester Support | |

Coupler A has the structure

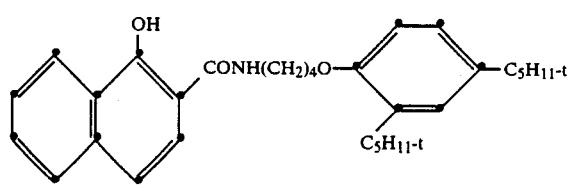

Coupler B has the structure

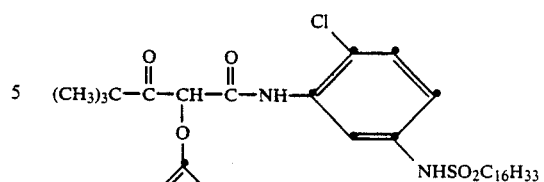

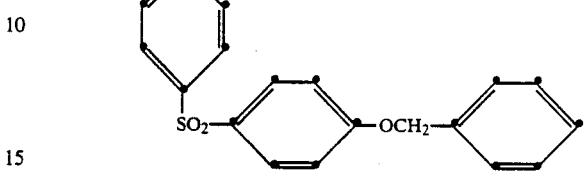

A series of elements containing the release compounds identified in Table 2, below, in the amounts shown in that table were prepared as indicated in (a) and (b) below, as was an element that differed only in that it contained no release compound.

a) Stepwise exposure through a green filter (Wratten #99) so that only the causer layer is exposed followed by processing at 38° C. as follows:

| Developer | 3'15" |
| Stop | 30" |
| Wash | 2' |
| Bleach | 3' |
| Wash | 3' |
| Fix | 4' |
| Wash | 3' |
| "Photoflow" Treatment | 30" |

The color developer composition was:

| Water | 800.0 mL |
| Potassium carbonate, anhydrous | 34.30 g |
| Potassium bicarbonate | 2.32 g |
| Sodium sulfite, anhydrous | 0.38 g |
| Sodium metabisulfite | 2.78 g |
| Potassium iodide | 1.20 mg |
| Sodium bromide | 1.31 g |
| Diethylenetriaminepentaacetic acid pentasodium salt (40% solution) (KODAK Anti-Calcium No. 8) | 8.43 g |
| Hydroxylamine sulfate (HAS) | 2.41 g |
| KODAK Color Developing Agent CD-4 (D-99) | 4.52 g |
| Water to make | 1.00 L |

From the stepwise exposures a D Log E curve is generated for each element. By comparison of the D Log E curve for the element which omitted the release compound with the D Log E curves for each of the elements containing a release compound, the suppression of contrast (γ) of the elements containing the release compound was calculated. This is shown in column (a) of Table 2.

b) Stepwise exposure through a minus blue filter (Wratten #12) so that both the causer and the receiver layers were exposed. The elements then were processed as in part a. Suppression of contrast (γ) for both layers is determined as in part a. These data are shown in column (b) of Table 2.

From column (a) it will be observed that inhibitor is being released, since as the amount of release compound incorporated is increased so is the suppression of contrast.

From column (b) it will be observed that there is migration of the inhibitor to an adjacent layer since there is suppression of contrast in the receiver layer, where no inhibitor releasing compound had been coated.

TABLE 2

| Release Coupler | Laydown (mg/m$^2$) | (a) % Causer γSuppression | (b) % Causer γSuppression | % Receiver γSuppression |
|---|---|---|---|---|
| Cpd. 17 | 54 | 26 | 33 | 17 |
|  | 108 | 55 | 57 | 33 |
|  | 215 | 65 | 65 | 49 |

The invention has been described in detail with particular reference to preferred embodiments thereof, but it will be understood that variations and modifications can be effected within the spirit and scope of the invention.

What is claimed is:

1. A photographic element comprising a support bearing a silver halide emulsion layer having associated therewith an image dye forming coupler and a release compound represented by the formula:

$$\begin{array}{c} CAR \\ | \\ TIME \\ | \\ PUG \end{array} \quad I$$

wherein

CAR is a carrier group from which the remainder of the molecule is released during photographic processing;

PUG is a photographically useful group; and

TIME is a timing group which is released from CAR during photographic processing and subsequently releases PUG, and contains a ring system represented by the structure:

[structure showing ring with Y, T, X$^1$, Q, X$^2$, Z$^1$, C, Z$^2$]

wherein
T is $$-\overset{|}{C}= \quad \text{or} \quad -\overset{|}{N}-;$$

Y is —O—, —S— or $$-\overset{R^1}{\underset{|}{N}}-;$$

when T is $$-\overset{|}{C}=;$$

and Y is $$-O-\overset{O}{\underset{\|}{C}}-, \quad -O-\overset{NR_1}{\underset{\|}{C}}-$$

or a covalent bond when T is $$-\overset{|}{N}-;$$

Q represents the atoms selected from carbon, nitrogen, oxygen, sulfur and phosphorus to complete a 5-, 6- or 7-membered carbocycle or heterocycle;

R$^1$ is COR$^2$ or SO$_2$R$^2$;

R$^2$ is alkyl or aryl;

each of Z$^1$ and Z$^2$ is individually hydrogen, alkyl, perfluoroalkyl, aryl, heterocyclyl, OR$^2$, SR$^2$, or N(R$^2$)$_2$;

each of X$^1$ and X$^2$ is individually a group as defined for Z$^1$ and Z$^2$ or represents the atoms selected from carbon, nitrogen, sulfur and phosphorus to complete a heterocyclic or non-aromatic carbocyclic ring system fused to the ring completed by Q;

with the proviso that each of X$^1$ and X$^2$ and each of Z$^1$ and Z$^2$ is not hydrogen at the same time.

2. A photographic element of claim 1 wherein PUG contains a nitrogen atom through which it is joined to TIME.

3. A photographic element of claim 1 wherein PUG is a development inhibitor.

4. A photographic element of claim 1 wherein PUG is a bleach accelerator.

5. A photographic element of claim 1 wherein PUG is an image dye.

6. A photographic element of claim 1 wherein TIME is cleaved from CAR during processing as a function of silver halide development.

7. A photograhic element of claim 1 wherein CAR is a coupler moiety.

8. A photographic element of claim 1 wherein CAR is a blocking group from which the remainder of the molecule is released in a nonimagewise manner under photographic processing conditions.

9. A photographic element of claim 8 wherein the blocking group releases the remainder of the molecule during a development step.

10. A photographic element of claim 1 wherein TIME comprises more than one timing group which sequentially release the remainder of the molecule after release from CAR.

11. A photographic element of claim 1 wherein each of X$^1$ and X$^2$ is individually a group as defined for Z$^1$ and Z$^2$.

12. A photographic element of claim 1 wherein CAR is a coupler moiety, TIME is joined to the coupling position of the coupler moiety and has the structure

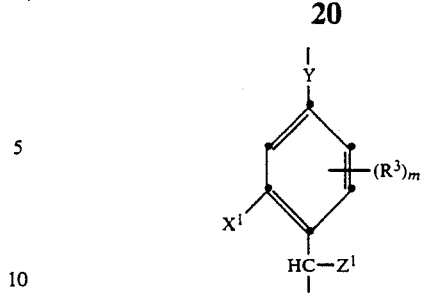
wherein
Y is —O— or —S—;
R³ is a non-interfering substituent selected from electron withdrawing groups and electron donating groups;
m is 0, 1, 2, or 3;
X¹ and Z¹ are independently alkyl, alkoxy, alkylthio, aryl, aryloxy, arylthio or heterocyclyl.
* * * * *

UNITED STATES PATENT AND TRADEMARK OFFICE
CERTIFICATE OF CORRECTION

PATENT NO. : 5,055,385　　　　　　　　　　　　　　Page 1 of 2
DATED    : October 9, 1991
INVENTOR(S) : Wojciech Slusarek, et al It is certified that error appears in the above-indentified patent and that said Letters Patent is hereby corrected as shown below:

On the title page:
The "Inventors" section, [75] "Wojciech Slusarek; John M. Buchanan; Philip T.S. Lau, all of Rochester, N.Y." should read --Wojciech Slusarek; John M. Buchanan; Philip T.S. Lau; David T. Southby, all of Rochester, N.Y.--

Column 2, Figure II, approximate line 15 reads:

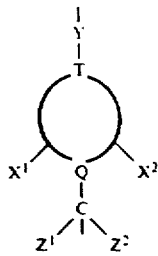      should read      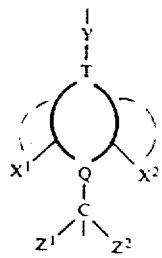

UNITED STATES PATENT AND TRADEMARK OFFICE
CERTIFICATE OF CORRECTION

PATENT NO. : 5,055,385
DATED : October 9, 1991
INVENTOR(S) : Wojciech Slusarek, et al It is certified that error appears in the above-indentified patent and that said Letters Patent is hereby corrected as shown below:

Column 17, approximate line 45 reads:

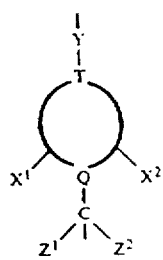  should read  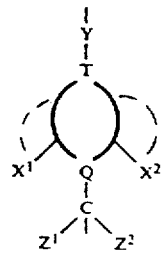

Signed and Sealed this

Twentieth Day of July, 1993

Attest:

MICHAEL K. KIRK

Attesting Officer

Acting Commissioner of Patents and Trademarks